United States Patent [19]

Yoshimoto et al.

[11] Patent Number: 4,851,445
[45] Date of Patent: Jul. 25, 1989

[54] N-(2-CHLORO-4-NITROPHENYL)-BENE-ZENE-SULFONAMIDE DERIVATIVE AND AGRICULTURAL FUNGICIDE CONTAINING SAME

[75] Inventors: Takeo Yoshimoto, Yokohama; Mitsumasa Umemoto, Ohmuta; Keiichi Igarashi, Musashino; Yutaka Kubota, Yokohama; Hideo Yamazaki, Yokohama; Yuji Enomoto, Yokohama; Hirohisa Yanagita, Chigasaki, all of Japan

[73] Assignee: Mitsui Toatsu Chemicals, Incorporated, Tokyo, Japan

[21] Appl. No.: 212,127

[22] Filed: Jun. 28, 1988

Related U.S. Application Data

[63] Continuation of Ser. No. 831,543, Feb. 21, 1986, abandoned.

[30] Foreign Application Priority Data

Feb. 27, 1985 [JP] Japan .................................... 60-36532
Mar. 1, 1985 [JP] Japan .................................... 60-38793

[51] Int. Cl.$^4$ ...................... C07C 143/78; A01N 41/06
[52] U.S. Cl. ........................................ 514/604; 564/92
[58] Field of Search ........................... 564/92; 514/604

[56] References Cited

U.S. PATENT DOCUMENTS

| 2,402,623 | 6/1946 | Hester | 564/92 |
| 2,853,519 | 9/1958 | Cook et al. | 564/92 |
| 3,034,955 | 5/1962 | Frick et al. | 564/92 X |
| 4,497,828 | 2/1985 | Yoshimoto et al. | 514/603 |
| 4,551,478 | 11/1985 | Yoshimato et al. | 514/603 |

FOREIGN PATENT DOCUMENTS

| 633391 | 12/1961 | Canada | 564/92 |
| 39-29571 | 12/1961 | Japan . | |
| 40-19199 | 8/1965 | Japan . | |
| 44-9304 | 4/1969 | Japan . | |
| 45-6836 | 3/1970 | Japan . | |
| 46-6797 | 2/1971 | Japan . | |
| 47-15119 | 5/1972 | Japan . | |
| 57-31655 | 2/1982 | Japan . | |

OTHER PUBLICATIONS

Journal of Agricultural and Food Chemistry, vol. 25, No. 1 (1977) pp. 81–83.
Linfield et al., *J. Med. Chem.*, 1983, 26(12), 1741–1746.

*Primary Examiner*—Charles F. Warren
*Assistant Examiner*—Carolyn S. Greason
*Attorney, Agent, or Firm*—Fisher, Christen & Sabol

[57] ABSTRACT

Disclosed herein are N-(2-chloro-4-nitrophenyl)benzenesulfonamide derivatives represented by the following general formula (I):

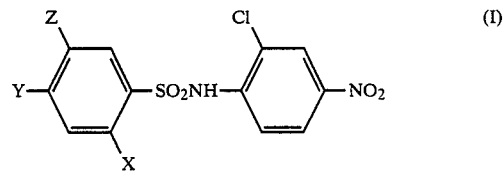

wherein X and Y individually mean a hydrogen or chlorine atom and Z denotes a chlorine atom or trifluoromethyl group, and agricultural fungicides containing said derivatives.

6 Claims, No Drawings

N-(2-CHLORO-4-NITROPHENYL)-BENEZENE-SULFONAMIDE DERIVATIVE AND AGRICULTURAL FUNGICIDE CONTAINING SAME

This application is a continuation of application Ser. No. 831,534, filed 2/21/86 abandoned.

BACKGROUND OF THE INVENTION (1) Field of the Invention

This invention relates to an N-(2-chloro-4-nitrophenyl)-benzenesulfonamide derivative represented by the following general formula (I):

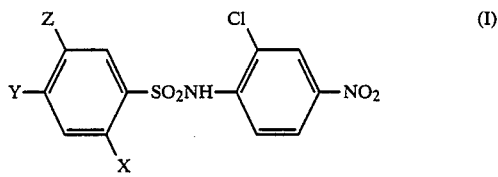

wherein X and Y individually mean a hydrogen or chlorine atom and Z denotes a chlorine atom or trifluromethyl group, and an agricultural fungicide containing said derivative as an active ingredient.

The above compound of this invention is useful as a soil fungicide for agriculture.

(2) Description of the Prior Art

Crop diseases have remained to date as one of serious problems for the cultivation of crops. Among such diseases, soil-borne diseases induced by pathogenic fungi in the soil (hereinafter called merely "soil-borne diseases" for the sake of brevity) are one of problems which are particularly difficult to solve. Recently, there are ever-increasing tendencies that vegetable culture areas are limited to certain specific districts and the same crops of commerce are cultivated continuously. For these tendencies, it has become more and more important to control such soil-borne diseases. It is however extremely difficult to control soil-borne diseases due to their nature. They hence tend to give more and more damages. For example, PCNB (pentachloronitrobenzene) has been used in some countries as a breakthrough fungicide against clubroot of cruciferous vegetables such as cabbages, Chinese cabbages, turnips, cauliflowers, broccolies and the like. It is applied so much that its application rate is said to be equivalent to fertilizers. In fields where cruciferous vegetables have been cultivated continuously, the standard application rate for PCNB is not enough to draw out its effects to satisfactory extents and it has hence become a common practice to apply in PCNB in much greater amounts. On the other hand, the environmental contamination by agricultural chemicals has staged up to a social problem and chemicals, which are being used in such large volumes as PCNB, would no longer be allowed. There is thus an extremely strong demand for chemicals which can exhibit their effects at lower application rates. It has virtually been considered to be difficult to achieve perfect chemical control on other soil-borne diseases, for example, powdery scab and scab of potatoes, rhizomania of sugar beets, virus diseases of small grains transmitted by Polymyxa, lettuce big vein, a soil-borne disease of radish, turnips, sugar beets, peas and the like, induced by various Aphanomyuces. Numerous sulfonamide-type compounds have been synthesized for many years and many researches have been conducted on their physiological activities. In the agricultural field, researches have been made on their applications as insecticides, no say nothing of their applications as herbicides and fungicides. For example, Japanese Patent Publication Nos. 29571/1964 and 19199/1965 may be referred to in connection with their applications as herbicides. As fungicides, may be mentioned Japanese Patent Publication Nos. 9304/1969, 6836/1970, 6797/1971 and 15119/1972, Japanese Patent Laid-Open No. 31655/1982, U.S. Pat. Nos. 4,497,828 and 4,551,478 and so on. On the other hand, U.S. Pat. No. 3,034,955 may be referred to regarding their applications as insecticides.

Compounds of the following formula are disclosed in U.S. Pat. No. 3,034,955.

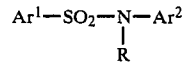

In the above formula, $Ar^1$ and $Ar^2$ are recited individually as a phenyl group which contains one or more substituents selected from hydrogen and halogen atoms and trifluoromethyl, nitro, alkyl and alkoxy groups. However, none of the compounds of this invention are included in the specific exemplary compounds disclosed in the specification of the U.S. patent. Further, this prior art publication refers merely to insecticidal activities of these compounds and contains no disclosure as to their use as fungicides. Although the compounds of this invention fall under the generic concept defined by the general formula of U.S. Pat. No. 3,034,955, the present invention is limited specifically to the N-(2-chloro-4-nitropheyl)-benzenesulfonamide derivatives of the specific structure indicated by the above general formula (I). Incidentally, the above prior art publication discloses 3-trifluoromethyl-4-chlorobenzene sulphonic acid-2'-nitro-4'-trifluoromethyl anilide [N-(2-nitro-4-trifluoromethylphenyl)-4-chloro-3-trifluoromethylbenzenesulfonamide] as a nitro group-containing compound. This compound is however apparently different from the compounds of this invention.

In U.S. Pat. Nos. 4,497,828 and 4,551,478, there are disclosed the controlling effects of certain sulfonamide derivatives against club root of cruciferous vegetables. All of the compounds disclosed in these U.S. patents are however limited to 3-nitrobenzenesulfonamide derivatives and the compounds of this invention are not disclosed at all. Moreover, the compounds of this invention are far superior to the compounds disclosed in the above U.S. patents in their controlling effects against clubroot.

The rest of the above-mentioned prior art publications neither disclose or suggest the application of the compounds of this invention as soil fungicides.

SUMMARY OF THE INVENTION

An object of this invention is to provide a fungicidal compound for soil-borne diseases, which compared with conventionally-known fungicides for soil-borne diseases, has a broader spectrum against soil-borne diseases, exhibits higher activities and hence shows effects at lower application rates and gives less influence to the environment.

Another object of this invention is to provide an agricultural fungicide containing the fungicidal compound as an active ingredient.

With a view toward achieving the above-described objects, the present inventors paid attention to the fact that sulfonamide derivatives have various physiological activities. They thus conducted an extensive research on sulfonamide derivatives. As a result, they have found certain compounds having broad spectra for various plant diseases, especially, soil-borne diseases against which no excellent controlling chemicals have yet been developed to date. Their spectra are so broad that they are by no means expectable from any known publications. They also have very highly fungicidal activity for soil-borne diseases. The above finding has led to completion of the present invention.

In one aspect of this invention, there is thus provided a novel N-(2-chloro-4-nitrophenyl)-benzenesulfonamide derivative represented by the following general formula (I):

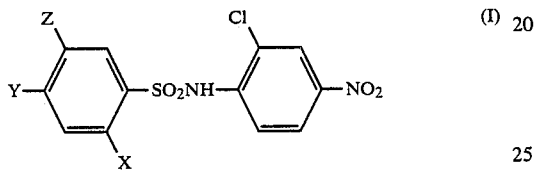

(I)

wherein X and Y individually mean a hydrogen or chlorine atom and Z denotes a chlorine atom or trifluoromethyl group.

In another aspect of this invention, there is also provided an agricultural fungicide comprising the N-(2-chloro-4-nitrophenyl)-benzenesulfonamide derivative of the above general formula (I) as an active ingredient.

The N-(2-chloro-4-nitrophenyl)-benzenesulfonamide derivative (I) of the present invention shows excellent controlling effects against clubroot of cruciferous vegetables such as cabbages, Chinese cabbages, turnips, cauliflowers, broccolis and the like, scab and powdery scab of potatoes and other soil-borne diseases induced by various Aphanomyces. Excellent controlling chemicals have been unavailable against these soil-borne diseases which have hence been considered as serious problems due to difficulties in their control. Some chemicals are available on the market but their effects are apparently inferior to those of the compound of this invention. The compound of this invention is therefore extremely useful as a soil fungicide.

Furthermore, the compound of this invention is also expected to show sufficient controlling effects against soil-borne diseases such as rhizomania of sugar beets, virus diseases of small grains transmitted by Polymyxa, etc.

The above and other objects, features and advantages of the present invention will become apparent from the following description and appended claims.

DETAILED DESCRIPTION OF THE INVENTION AND PREFERRED EMBODIMENTS

The compounds of this invention are clearly different in structure from the compounds disclosed in U.S. Pat. Nos. 4,497,828 and 4,551,478. As apparent also from the above-described prior art, sulfonamide derivatives show various different physiological activities depending on their structural differences. It is absolutely impossible to predict from the above-described prior art that the compounds of this invention have broad spectra and highly-active controlling effects against soil-borne diseases.

Each of the compounds (I) of this invention can be synthesized by a reaction which is represented by the following equation:

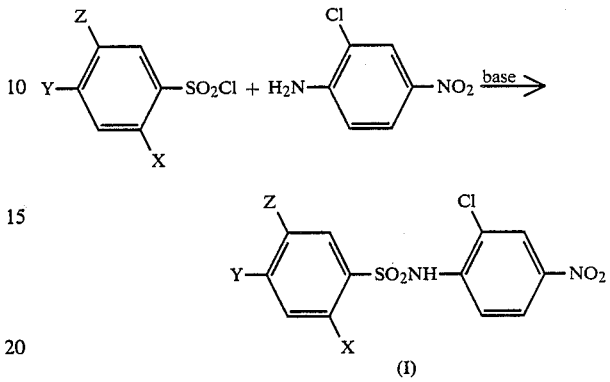

wherein X and Y mean individually a hydrogen or chlorine atom and Z denotes a chlorine atom or trifluoromethyl group.

As exemplary bases useful in the practice of the above reaction, may be mentioned pyridine, triethylamine, trimethylamine and the like with pyridine being most suitable. As a reaction solvent, it is possible to use an inert organic solvent, for example, an aromatic hydrocarbon such as toluene, xylene, chlorobenzene, dichlorobenzene or the like. Of these, those having boiling points above 110° C. are suitable. The reaction temperature and reaction time vary depending on a solvent to be used. It is however desirous to carry out the reaction at 110°–180° C. for 5–15 hours.

The compounds of this invention exhibit antifungal activities and multiplication inhibitory effects against various plant pathogenic fungi and may be applied to a wide range of plant diseases. They show outstanding effects, especially, against soil-borne diseases of various crops, for which effective controlling chemicals have not been furnished to date. For example, they exhibit excellent controlling effects against clubroot of cruciferous vegetables such as cabbages, Chinese cabbages, turnips, cauliflowers, broccolies and the like, scab and powdery scab of potatoes, rhizomania of sugar beets, virus diseases of small grains transmitted by Polymyxa, soil-borne diseases of sugar beets, radish, turnips, peas and the like induced by avarious Aphanomyces, lettus big vein, etc. With respect to bacteria, they have antibacterial activities especially against gram-positive bacteria.

When the compounds of this invention are used as soil treatment agents, they are effective at application rates in a range of 0.2–40 kg per hectare or preferably 0.5–20 kg per hectare on average although their application rates vary depending on the type of each target disease and other conditions, for example, soil conditions (pH, water content, content of organic matter, etc.) and weather conditions.

The compounds of this invention may be used neat. However, they are usually added and mixed with a carrier and if necessary, one or more other adjuvants and are then prepared into applicable formulations for their use, e.g., dusts, wettable powders, granules, flowable formulations and the like. As exemplary carriers, may be mentioned inorganic materials such as clays, talc, bentonite, calcium carbonate, diatomaceous earth, zeolite and silicic anhydride, plant-originated organic materials such as wheat flour, soybean meal, starch and crystalline cellulose, high-molecular compounds such as petroleum resins, polyvinyl chloride and polyalkylene glycols, urea, waxes and so on.

If necessary, it is also possible to use adjuvants which are required for preparing applicable formulations, for example, wetting agent, dispersant, stickener, spreading and sticking agent and the like. They may be suitably used either singly or in combination. As adjuvants useful for wetting, dispersing, spreading, component-stabilizing and/or rust-inhibiting purposes, may be mentioned various surfactants, high-molecular compounds such as gelatin, albumin, sodium aluginate, methylcellulose, carboxymethylcellulose, polyvinyl alcohol and xanthan gum, and other adjuvants. Illustrative of surfactants may include non-ionic surfactants such as polymerization products of alkylphenols, higher alcohols, alkylnaphthols, higher fatty acids, fatty acid esters, dialkylphosphonic amines or the like with ethylene oxide or with ethylene oxide and propylene oxide; anionic surfactants such as alkylsulfates such as sodium laurylsulfate, alkylsulfonates such as sodium 2-ethylhexylsulfonate, and arylsulfonates such as sodium lignosulfonate and sodium dodecylbenzenesulfonate; and various cationic and amphoteric surfactants.

When the compounds of this invention are used as fungicides, it is possible to prepare them, into applicable formulations, together with other agricultural chemicals, for example, insecticides, fungicides, acaricides, nematicides, anti-viruses, herbicides, plant growth regulators and/or attractants, soil conditioning materials such as lime and/or fertilizing materials, to say nothing of applying them along with one or more of the abovementioned agricultural chemicals, soil conditioning materials and fertilizing materials.

Various applicable formulations or sprayable or spreadable preparations, which contain the compounds of this invention, may be applied by methods which are routinely followed. They may be applied, for example, by spraying or spreading methods (for example, dusting, granular application, spraying as liquid formulations), soil surface application, soil incorporation, surface application (for example, coating, powdering, covering), seed dipping, plant root powdering, root dipping, etc. The desirable contents of the active ingredient in various preparation forms are generally 0.1–10 wt.% in dust, 5–90 wt.% in wettable powder, 0.1–10 wt.% in granules, and 20–90 wt.% in flowable formulation.

EXAMPLES

The synthesis of certain compounds of this invention will hereinafter be described in detail by the following specific Synthesis Examples and specific examples of the compound of this invention and their physical data will be summarized in Table 1.

SYNTHESIS EXAMPLE 1

Synthesis of N-(2-chloro-4-nitrophenyl)-3-trifluromethylbenzenesulfonamide (Compound 1)

In a 400 ml flask, 200 ml of o-dichlorobenzene, 1 ml of pyridine and 1.7 g (0.01 mole) of 2-chloro-4-nitroaniline were charged. While stirring the contents at room temperature, 2.5 g (0.01 mole) of 3-trifluoromethylbenzenesulfonylchloride was added gradually over 30 minutes. Thereafter, the reaction mixture was heated and stirred for 8 hours under reflux (175°–180° C.) to complete the reaction. After cooling the reaction mixture to room temperature, it was thoroughly washed first with dilute hydrochloric acid and then with water. Subsequent to its dehydration with sodium sulfate, o-dichlorobenzene was distilled off under reduced pressure. The residue was subjected to silica gel chromatography (eluent: benzene) to isolate the intended Compound 1. m.p. 126°–127° C., yield 1.9 g (50%).

SYNTHESIS EXAMPLE 2

Synthesis of N-(2-chloro-4-nitrophenyl)-4-chloro-3-trifuoromethylbenzenesulfonamide (Compound 3)

In a 400 ml flask, 200 ml of o-xylene, 1 ml of pyridine and 1.7 g (0.01 mole) of 2-chloro-4-nitroaniline were charged. While stirring the contents at room temperature, 2.8 g (0.01 mole) of 4-chloro-3-trifluoromethylbenzenesulfonylchloride was added dropwise at room temperature over 30 minutes. Thereafter, the reaction mixture was heated and stirred for 10 hours under reflux (140°–145° C.). After cooling the reaction mixture to room temperature, it was thoroughly washed first with dilute hydrochloric acid and then with water. Subsequent to its dehydration with anhydrous sodium sulfate, o-xylene was distilled off under reduced pressure. The residue was subjected to silica gel chromatography (eluent: benzene) to isolate the intended Compound 3. m.p. 156°–158° C., yield 2.3 g (55%).

SYNTHESIS EXAMPLE 3

Synthesis of N-(2-chloro-4-nitrophenyl)-3,4-dichlorobenzenesulfonamide (Compound 5)

Following the procedure of Synthesis Example 2, the intended Compound 5 was obtained by using 1.7 g (0.01 mole) of 2-chloro-4-nitroaniline and 2.5 g (0.01 mole) of 3,4-dichlorobenzenesulfonylchloride. Its purification was however effected by its recrystallization from acetic acid. m.p. 199°–201° C., yield 3.0 g (79%).

SYNTHESIS EXAMPLE 4

Synthesis of N-(2-chloro-4-nitrophenyl)-2,4,5-trichlorobenzenesulfonamide (Compound 6)

Following the procedure of Synthesis Example 1, the intended Compound 6 was obtained by using 1.7 g (0.01 mole) of 2-chloro-4-nitroaniline and 2.8 g (0.01 mole) of 2,4,5-trichlorobenzenesulfonylchloride. Its purification was however effected by its recrystallization from ethanol. m.p. 177°–179° C., yield 3.5 g (84%).

Other compounds were also synthesized following the above-described procedures.

TABLE 1

N—(2-Chloro-4-Nitrophenyl)-Benzenesulfonamide Derivatives

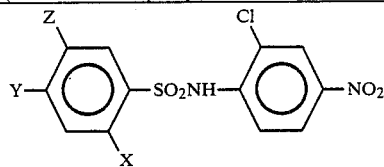

| Comp'd No. | Formula (I) X | Y | Z | Elementary analysis (%), found/(calculated) C | H | Cl | F | N | S | m.p. (°C.) | IR absorption spectrum $\nu_{max}^{KBr}$ (cm$^{-1}$) |
|---|---|---|---|---|---|---|---|---|---|---|---|
| 1 | H | H | CF$_3$ | 41.35 (41.00) | 2.02 2.10 | 9.23 9.33 | 14.76 14.98 | 7.30 7.36 | 8.37 8.41) | 126–127 | 3340 (—NH—) |
| 2 | Cl | H | CF$_3$ | 37.41 (37.59) | 1.54 1.69 | 17.24 17.11 | 13.81 13.73 | 6.68 6.75 | 7.69 7.71) | 167–169 | 3340 (—NH—) |
| 3 | H | Cl | CF$_3$ | 37.64 (37.59) | 1.74 1.69 | 17.05 17.11 | 13.54 13.73 | 6.80 6.75 | 7.74 7.71) | 156–158 | 3340 (—NH—) |
| 4 | Cl | H | Cl | 37.78 (37.74) | 1.87 1.83 | 27.87 27.92 | — — | 7.30 7.34 | 8.35 8.39) | 184–185 | 3280 (—NH—) |
| 5 | H | Cl | Cl | 37.71 (37.74) | 1.80 1.83 | 27.98 27.92 | — — | 7.30 7.34 | 8.31 8.39) | 199–201 | 3330 (—NH—) |
| 6 | Cl | Cl | Cl | 34.48 (34.62) | 1.66 1.44 | 34.04 34.14 | — — | 6.67 6.73 | 7.75 7.69) | 177–179 | 3290 (—NH—) |

Exemplary fungicidal formulations containing compounds of this invention as active ingredients will next be described in the following Formulation Examples. It should however be borne in mind that the types and proportions of adjuvants are not limited to those employed in the following Formulation Examples.

Formulation Example 1: (Dust)

A dust containing 3 wt.% of Compound 1 as an active ingredient was obtained by mixing and grinding 3 parts by weight of Compound 1, 10 parts by weight of "Carplex #80" (trademark for white carbon; product of Shionogi & Co., Ltd.) and 87 parts by weight of clay.

Formulation Example 2: (Dusts)

Dusts containing 3 wt.% of Compounds 2–6 respectively as active ingredients were obtained by preparing the respective compounds in accordance with the procedure of Formulation Example 1.

Formulation Example 3: (Dust)

A dust containing 0.5 wt.% of Compound 1 as an active ingredient was obtained by mixing and grinding 0.5 parts by weight of Compound 1, 49.5 parts by weight of calcium carbonate and 50 parts by weight of clay.

Formulation Example 4: (Dusts)

Dusts containing 0.5 wt.% of Compounds 2–6 respectively as active ingredients were obtained by preparing the respective compounds in accordance with the procedure of Formulation Example 3.

Formulation Example 5: (Dust)

A dust containing 1 wt.% of Compound 1 as an active ingredient was obtained by mixing and grinding 1 part by weight of Compound 1, 5 parts by weight of "Adeka Estol EX-1303" (trademark for higher fatty acid ester composition; drift inhibitor; product of Asahi Denka Kogyo K.K.), 44 parts by weight of calcium carbonate and 50 parts by weight of clay.

Formulation Example 6: (Dusts)

Dusts containing 1 wt.% of Compounds 2–6 respectively as active ingredients were obtained by preparing 1 part by weight of the respective compounds in accordance with the procedure of Formulation Example 5.

Formulation Example 7: (Wettable Powder)

A wettable powder containing 50 wt.% of Compound 1 as an active ingredient was obtained by intimately grinding and mixing 50 parts by weight of Compound 1, 5 parts by weight of "Sorpol" (trade mark for a surfactant; product of Toho Chemical Industry Co., Ltd.) and 45 parts by weight of "Radiolite" (trade mark for calcined diatomaceous earth; product of Showa Chemicals Inc.).

Formulation Example 8: (Wettable powders)

Wettable powders containing 50 wt.% of Compounds 2–6 respectively as active ingredients were obtained by preparing 50 parts by weight of the respective compounds in accordance with the procedure of Formulation Example 7.

Formulation Example 9: (Wettable Powder)

A wettable powder containing 10 wt.% of Compound 1 as an active ingredient was obtained by intimately grinding and mixing 10 parts by weight of Compound 1, 10 parts by weight of "Carplex #80" (trademark for white carbon; product of Shionogi & Co., Ltd.), 3 parts by weight of "Emal 10" (trademark for a surfactant; product of Kao Corporation) and 77 parts by weight of clay.

Formulation Example 10: (Wettable powders)

Wettable powders containing 10 wt.% of Compounds 2–6 respectively as active ingredients were obtained by preparing 10 parts by weight of the respective compounds in accordance with the procedure of Formulation Example 9.

Formulation Example 11: (Wettable Powder)

A wettable powder containing 50 wt.% of Compound 1 as an active ingredient was obtained by intimately grinding and mixing 50 parts by weight of Compound 1, 10 parts by weight of "Carplex #80" (trademark for white carbon; product of Shionogi & Co., Ltd.), 4 parts by weight of "Emal 10" (trademark for a surfactant; product of Kao Corporation) and 36 parts by weight of "Radiolite".

Formulation Example 12: (Wettable powders)

Wettable powders containing 50 wt.% of Compounds 2-6 respectively as active ingredients were obtained by preparing 50 parts by weight of the respective compounds in accordance with the procedure of Formulation Example 7.

Formulation Example 13: (Granule)

Granules containing 1 wt.% of Compound 1 as an active ingredient was obtained by intimately mixing 1 part by weight of Compound 1, 2 parts by weight of sodium dodecylbenzenesulfonate, 1 part by weight of sodium lignosulfonate, 25 parts by weight of talc and 71 parts by weight of bentonite, adding water to the mixture and kneading the resultant mass, granulating the thus-kneaded mass by means of an extrusion-granulating machine and then drying the granule.

Formulation Example 14: (Granule)

Granules containing 1 wt.% of Compounds 2-6 respectively as active ingredients were obtained by preparing 1 parts by weight of the respective compounds in accordance with the procedure of Formulation Example 13.

Formulation Example 15: (Granule)

Granule containing 3 wt.% of Compound 1 as an active ingredient was obtained by intimately mixing 96 parts by weight of granular calcium carbonate and 1 part by weight of "Adeka Estol EX-1303" (trademark for higher fatty acid ester composition; drift inhibitor; product of Asahi Denka Kogyo K.K.) and then adding and mixing 3 parts of ground Compound 1 with the resultant mixture.

Formulation Example 16: (Granules)

Granules containing 3 wt.% of Compounds 2-6 respectively as active ingredients were obtained by preparing 3 parts by weight of the respective compounds in accordance with the procedure of Formulation Example 15.

Formulation Example 17: (Fertilizer-Mixed Granule)

A fertilizer-mixed granule containing 2 wt.% of Compound 1 as an active ingredient was obtained by intimately mixing 97 parts by weight of a granular compound fertilizer and 1 part by weight of "Driless A" (trademark for higher fatty acid ester composition; drift inhibitor; product of Sankyo Co., Ltd.) and then adding and mixing 2 parts by weight of Compound 1. Formulation Example 18: (Fertilizer-Mixed Granules)

Fertilizer-mixed granules containing 2 wt.% of Compounds 2-6 respectively as active ingredients were obtained by preparing 2 parts by weight of Compounds 2-6 in accordance with Formulation Example 17.

Formulation Example 19: (Fertilizer-Mixed Granule)

A fertilizer-mixed granule containing 6 wt.% of Compound 1 as an active ingredient was obtained by intimately mixing 92 parts by weight of a granular compound fertilizer and 2 parts by weight of "Adeka Estol EX-1303" (trademark for higher fatty acid ester composition; drift inhibitor; product of Asahi Denka Kogyo, K.K.) and then adding and mixing 6 parts by weight of Compound 1.

Formulation Example 20: (Fertilizer-Mixed Granules)

Fertilizer-mixed granules containing 6 wt.% of Compounds 2-6 respectively as active ingredients were obtained by preparing 6 parts by weight of Compounds 2-6 in accordance with Formulation Example 19.

Formulation Example 21: (Flowable Formulation)

A flowable formulation containing 40 wt.% of Compound 1 as an active ingredient was obtained by adding 50 parts by weight of water to a mixture of 50 parts by weight of Compound 1, 9 parts by weight of sodium lignosulfonate and 1 part by weight of gum arabic and then mixing and finely grinding them by means of a sand grinder.

Formulation Example 22: (Flowable Formulations)

Flowable formulations containing 40 wt.% of Compounds 2-6 respectively as active ingredients were obtained by preparing 40 parts by weight of Compounds 2-6 in accordance with Formulation Example 21.

Effects of certain compounds of this invention and agricultural fungicides containing same for controlling soil-borne diseases will next be described specifically by the following Tests.

Test 1: (Controlling Test of Clubroot of Chinese Cabbage)

After adding and mixing a prescribed amount of a dust, which had been prepared in accordance with Formulation Example 1, with 1 kg of soil contaminated with clubroot (*Plasmodiophora brassicae*) of cruciferous vegetables, the thus-treated soil was filled in an unglazed pot having a diameter of 15 cm. Twenty seeds of Chinese cabbage (variety: Muso) were planted there. The resultant seedlings were allowed to grow in a green house. In the 6th week after the planting, an investigation was carried out to determine whether diseases had occured on their root sections. Its controlling effects were expressed by calculating its control value in accordance with the following equation. Results are shown in Table 2 and Table 3.

$$\text{Control value (\%)} = \frac{\text{Number of intact seedlings}}{\text{Number of investigated seedlings}} \times 100$$

TABLE 2

| Sample compound | Amount of active ingredient per pot (mg) | | | |
|---|---|---|---|---|
| | 2.5 | 5 | 10 | 20 |
| 1 | 93% | 100% | 100% | 100% |
| 2 | 98 | 100 | 100 | 100 |
| 3 | 100 | 100 | 100 | 100 |
| Control A[1] | 0 | 0 | 30 | 45 |
| Control B[2] | 60 | 75 | 100 | 100 |
| Untreated | 0 | | | |

[1]Pentachloronitrobenzene (commercial product).
[2]N—(2-Chloro-4-nitrophenyl)-4-methyl-3-nitrobenzenesulfonamide (U.S. Pat. No. 4,497,828).

TABLE 3

| Sample compound | Amount of active ingredient per pot (mg) | | | |
|---|---|---|---|---|
| | 2.5 | 5 | 10 | 20 |
| 4 | 90% | 100% | 100% | 100% |
| 5 | 95 | 100 | 100 | 100 |

TABLE 3-continued

| Sample compound | Amount of active ingredient per pot (mg) | | | |
|---|---|---|---|---|
| | 2.5 | 5 | 10 | 20 |
| 6 | 88 | 100 | 100 | 100 |
| Control A[1] | 0 | 0 | 31 | 70 |
| Control B[2] | 31 | 70 | 98 | 100 |
| Untreated | | 3 | | |

[1]Pentachloronitrobenzene (commercial product).
[2]N—(2-Chloro-4-nitrophenyl)-4-methyl-3-nitrobenzenesulfonamide (U.S. Pat. No. 4,497,828).

Test 2: (Controlling Test of Damping-Off of Japanese Turnips by *Aphanomyces raphani*)

A prescribed amount of a dust prepared in accordance with the procedure of Formulation Example 2 was added to 1 kg of sterilized soil. After thoroughly mixing the dust with the soil, the soil was filled in an unglazed pot having a diameter of 15 cm. Then, twenty seeds of Japanese turnips (variety: Shinbansei Komatsuna) were planted there. Five days later from the planting, the soil was drenched with a zoospore suspension of *Aphanomyces raphani* (50 zoospores per field of vision, multiplication: ×50), which had been prepared in advance, in an amount of 50 ml per pot, thereby inoculating *Aphanomyces raphani* to the soil. The Japanese turnips were allowed to grow for 30 days in a green house and were then inspected from one to another to determine whether the disease had been developed or not. The controlling effects were expressed in terms of control value which has been defined in Test 1. The test was conducted with 3 replications.

Results are shown as average values of the 3 replications in Table 4 and Table 5.

TABLE 4

| Sample compound | Amount of active ingredient per pot (mg) | | |
|---|---|---|---|
| | 2.5 | 5 | 10 |
| 1 | 80% | 85% | 100% |
| 2 | 75 | 88 | 100 |
| 3 | 90 | 95 | 100 |
| Control A[1] | 0 | 20 | 40 |
| Control C[2] | 0 | 18 | 26 |
| Control D[3] | 0 | 21 | 35 |
| Untreated | | 0 | |

[1]Pentachloronitrobenzene (commercial product).
[2]N—(4-Chlorophenyl)-3-nitrobenzenesulfonamide (Japanese Patent Publication No. 15119/1972).
[3]N—(3,4-Dichlorophenyl)-3-nitrobenzenesulfonamide (Japanese Patent Publication No. 15119/1972).

TABLE 5

| Sample compound | Amount of active ingredient per pot (mg) | | |
|---|---|---|---|
| | 2.5 | 5 | 10 |
| 4 | 63% | 84% | 100% |
| 5 | 52 | 81 | 100 |
| 6 | 58 | 90 | 100 |
| Control A[1] | 0 | 0 | 36 |
| Control C[2] | 0 | 13 | 26 |
| Control E[4] | 0 | 21 | 40 |
| Untreated | | 0 | |

[1]Pentachloronitrobenzene (commercial product).
[2]N—(4-Chlorophenyl)-3-nitrobenzenesulfonamide (Japanese Patent Publication No. 15119/1972).
[4]N—(2-Chloro-4-nitrophenyl)-3-nitrobenzenesulfonamide (U.S. Pat. No. 4,551,478).

Test 3: (Controlling Test of Root Rot of Peas)

To 1 kg of soil contaminated by the pathogenic fungi, *Aphanomyces euteiches*, for root rot of peas, a prescribed amount of a dust prepared in accordance with the procedure of Formation Example 3 was added. They were then thoroughly mixed together. The soil was then filled in an unglazed pot having a diameter of 15 cm, to which ten seeds of peas were planted. The peas were allowed to grow in a green house. On the 30th day after the planting, their roots were pulled out to inspect and evaluate the degree of lesion. The controlling effects were expressed on a scale of 4, which ranged from 0 to 3. The rankings were then expressed in terms of lesion degree in accordance with the following equation. The test was conducted with 3 replications. Results are shown as average values in Table 6 and Table 7.

| Lesion index | |
|---|---|
| 0 | no disease |
| 1 | some browning near the ground |
| 2 | severe browning near the ground |
| 3 | death or nearly death |

$$\text{Lesion degree} = \frac{\Sigma(\text{Each index} \times \text{number of plants})}{3 \times \text{total number of investigated plants}} \times 100$$

TABLE 6

| Sample compound | Amount of active ingredient per pot (mg) | | |
|---|---|---|---|
| | 2.5 | 5 | 10 |
| 1 | 20.0 | 3.4 | 3.4 |
| 2 | 12.3 | 10.0 | 9.0 |
| 3 | 20.4 | 5.8 | 4.0 |
| Control D[1] | 52.3 | 52.3 | 46.8 |
| Control F[2] | 45.4 | 54.3 | 48.2 |
| Control G[3] | 58.3 | 46.4 | 45.8 |
| Untreated | | 60.2 | |

[1]N—(3,4-Dichlorophenyl)-3-nitrobenzenesulfonamide (Japanese Patent Publication No. 15119/1972).
[2]N—(3,4-Dichlorophenyl)-3,4-dichlorobenzenesulfonamide (Japanese Patent Publication No. 6797/1971).
[3]Hydroxyisoxazole (commercial product).

TABLE 7

| Sample compound | Amount of active ingredient per pot (mg) | | |
|---|---|---|---|
| | 2.5 | 5 | 10 |
| 4 | 10.8 | 4.3 | 2.1 |
| 5 | 11.3 | 5.5 | 3.0 |
| 6 | 12.7 | 6.0 | 2.8 |
| Control C[4] | 50.3 | 51.4 | 40.8 |
| Control E[5] | 60.5 | 54.3 | 43.2 |
| Control G[3] | 49.8 | 51.3 | 45.3 |
| Untreated | | 58.2 | |

[3]Hydroxyisoxazole (commercial product).
[4]N—(4-Chlorophenyl)-3-nitrobenzenesulfonamide (Japanese Patent Publication No. 15119/1972).
[5]N—(2-Chloro-4-nitrophenyl)-3-nitrobenzenesulfonamide (U.S. Pat. No. 4,551,478).

Test 4: (Controlling Test of Damping-Off of Sugar Beets)

A prescribed amount of a dust prepared in accordance with the procedure of Formulation Example 2 was added to 1 kg of sterilized soil. After thoroughly mixing the dust with the soil, the soil was filled in an unglazed pot having a diameter of 15 cm. Then, twenty seeds of sugar beets (variety: Monohill) were planted there. Three days after, the soil was inoculated with a zoosphere suspension of *Aphanomyces raphani* (50 zoospores per field of vision, multiplication: ×150), which had been prepared in advance, in an amount of 50 ml per pot. The sugar beets were allowed to grow in a green house. On the 10th day after the inoculation, the state of growth of the young seedlings were inspected and evaluated. The control value was calculated in accordance with the following equation. Results are shown in Table 8 and Table 9.

$$\text{Control value (\%)} = \frac{\text{Number of intact seedlings}}{\text{Number of investigated seedlings}} \times 100$$

TABLE 8

| Sample compound | Amount of active ingredient per pot (mg) | | |
|---|---|---|---|
| | 2.5 | 5 | 10 |
| 1 | 60.5% | 80.0% | 85.3% |
| 2 | 58.6 | 79.8 | 90.5 |
| 3 | 75.0 | 83.0 | 90.8 |
| Control D[1] | 0.0 | 11.2 | 20.3 |
| Control F[2] | 0.0 | 15.0 | 25.4 |
| Control G[3] | 15.3 | 75.0 | 80.0 |
| Untreated | | 0.0 | |

[1]N—(3,4-Dichlorophenyl)-3-nitrobenzenesulfonamide (Japanese Patent Publication No. 15119/1972).
[2]N—(3,4-Dichlorophenyl)-3,4-dichlrobenzenesulfonamide (Japanese Patent Publication No. 6797/1971).
[3]Hydroxyisoxazole (commercial product).

TABLE 9

| Sample compound | Amount of active ingredient per pot (mg) | | |
|---|---|---|---|
| | 2.5 | 5 | 10 |
| 4 | 78% | 94% | 100% |
| 5 | 85 | 97 | 100 |
| 6 | 82 | 93 | 100 |
| Control C[4] | 2 | 13 | 21 |
| Control E[5] | 0 | 14 | 24 |
| Control G[3] | 18 | 70 | 85 |
| Untreated | | 0 | |

[3]Hydroxyisoxazole (commercial product).
[4]N—(4-Chlorophenyl)-3-nitrobenzenesulfonamide (Japanese Patent Publication No. 15119/1972).
[5]N—(2-Chloro-4-nitrophenyl)-3-nitrobenzenesulfonamide (U.S. Pat. No. 4,551,478).

Test 5: (Controlling Test of Scab of Potatoes)

Pathogenic fungi for potatoes scab, which had in advance been cultured in a liquid oatmeal culture medium, were mixed in soil to prepare contaminated soil. A prescribed amount of a dust prepared in accordance with the procedure of Formulation Example 2 was then added to 8 kg of the contaminated soil. After thoroughly mixing the dust and contaminated soil, the soil was filled in a resin pot of 1/2,000 are and potatoes (variety: Danshaku) were planted there. The potatoes were allowed to grow outdoors. On the 80th day after the planting, tubers were dug up to investigate the state of lesion. The investigation was visually conducted on a scale of 5, which ranged from 0 to 4, with respect to tubers each of about 20 g or heavier. The lesion degree was calculated in accordance with the following equation to determine the controlling effects. Results are shown in Table 10 and Table 11.

| Lesion index | |
|---|---|
| 0 | no lesion |
| 1 | 1–3 lesions or not broader than 3% infected areas. |
| 2 | 4–10 lesions or 4–13% infected area. |
| 3 | 11–20 lesions or 14–25% infected area. |
| 4 | 21 or more lesions or 26% or more infected area. |

$$\text{Lesion degree} = \frac{\Sigma(\text{Each index} \times \text{number of tubers})}{4 \times \text{total number of investigated tubers}} \times 100$$

TABLE 10

| Sample compound | Amount of active ingredient (kg/ha) | Lesion degree |
|---|---|---|
| 1 | 6 | 10.3 |
| 2 | 6 | 6.5 |
| 3 | 6 | 5.1 |
| Control A[1] | 80 | 20.0 |
| Control C[2] | 6 | 28.3 |
| Control H[3] | 6 | 36.5 |
| Untreated | — | 46.9 |

[1]Pentachloronitrobenzene (commercial product).
[2]N—(4-Chlorophenyl)-3-nitrobenzenesulfonamide (Japanese Patent Publication No. 15119/1972).
[3]N—(3,4-Dichlorophenyl)-3,4-dichlorobenzenesulfonamide (Japanese Patent Publication No. 6797/1971).

TABLE 11

| Sample compound | Amount of active ingredient (kg/ha) | Lesion degree |
|---|---|---|
| 4 | 10 | 5.8 |
| 5 | 10 | 6.5 |
| 6 | 10 | 4.6 |
| Control A[1] | 80 | 21.3 |
| Control C[2] | 10 | 30.0 |
| Control E[4] | 10 | 29.4 |
| Untreated | — | 48.3 |

[1]Pentachloronitrobenzene (commercial product).
[2]N—(4-Chlorophenyl)-3-nitrobenzenesulfonamide (Japanese Patent Publication No. 15119/1972).
[4]N—(2-Chloro-4-nitrophenyl)-3-nitrobenzenesulfonamide (U.S. Pat. No. 4,551,478)

From the above description, it is clear that the compounds of this invention and agricultural fungicides containing them are excellent fungicidal compounds and compositions for soil-borne diseases, which have broader spectra and higher activities, exhibit their effects at lower application rates and hence give less adverse influence to the environment than conventionally-known fungicides for soil-borne diseases.

Having now fully described the invention, it will be apparent to one of ordinary skill in the art that many changes and modifications can be made thereto without departing from the spirit or scope of the invention as set forth herein.

We claim:

1. N-(2-chloro-4-nitrophenyl)-2,4,5-trichlorobenzenesulfonamide.

2. An agricultural soil fungicidal composition comprising (a), as an active ingredient, 0.1 to 90 percent by weight of N-(2-chloro-4-nitrophenyl)-2,4,5-trichlorobenzenesulfonamide and (b) a carrier.

3. Combination of the agricultural soil fungicidal composition of claim 2 and another agricultural chemical selected from the group consisting of an insecticide, a fungicide, an acaricide, a nematicide, an anti-virial compound, a herbicide, a plant growth regulator and an attractant.

4. Combination of claim 3 wherein at least one soil conditioning material, wetting agent, dispersant, spreading agent, sticking agent, component-stabilizing agent and/or rust-inhibiting agent is also present.

5. Agricultural soil fungicidal composition of claim 3 wherein said carrier is clay, talc, bentonite, calcium carbonate, diatomaceous earth, zeolite, silicic anhydride, wheat flour, soybean meal, starch, crystalline cellulose, petroleum resin, polyvinyl chloride, polyalkylene glycol, urea or wax.

6. Agricultural soil fungicidal composition of claim 3 which is in the form of a dust, a wettable powder, granules or a flowable formulation.

* * * * *